(12) United States Patent
Toyoda et al.

(10) Patent No.: US 9,962,232 B2
(45) Date of Patent: May 8, 2018

(54) MEDICAL SUPPORT DEVICE

(71) Applicant: DENSO CORPORATION, Kariya, Aichi-pref. (JP)

(72) Inventors: Kazutaka Toyoda, Kariya (JP); Tsuyoshi Ueyama, Kariya (JP); Go Mukumoto, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 0 days. days.

(21) Appl. No.: 15/393,293

(22) Filed: Dec. 29, 2016

(65) Prior Publication Data

US 2017/0196654 A1    Jul. 13, 2017

(30) Foreign Application Priority Data

Jan. 8, 2016   (JP) ................................. 2016-002505

(51) Int. Cl.

| | |
|---|---|
| *A61B 90/50* | (2016.01) |
| *A61B 34/00* | (2016.01) |
| *A61B 17/16* | (2006.01) |
| *A61G 15/16* | (2006.01) |
| *A61B 34/20* | (2016.01) |
| *A61B 90/00* | (2016.01) |
| *A61B 17/00* | (2006.01) |
| *A61C 1/00* | (2006.01) |
| *A61C 8/00* | (2006.01) |

(52) U.S. Cl.
CPC .......... *A61B 90/50* (2016.02); *A61B 17/1673* (2013.01); *A61B 34/77* (2016.02); *A61G 15/16* (2013.01); *A61B 2017/00123* (2013.01); *A61B 2034/2059* (2016.02); *A61B 2090/064* (2016.02); *A61C 1/0015* (2013.01); *A61C 8/0089* (2013.01)

(58) Field of Classification Search
CPC ..... A61B 90/50; A61B 34/77; A61B 17/1673; A61B 2034/2059; A61B 2090/064; A61B 2017/00123; A61C 8/0089; A61C 1/0015; A61G 15/16

See application file for complete search history.

(56) References Cited

U.S. PATENT DOCUMENTS

| | | | | |
|---|---|---|---|---|
| 3,805,388 A | * | 4/1974 | Kato ...................... | A61G 15/16 433/79 |
| 5,343,391 A | * | 8/1994 | Mushabac .......... | A61C 13/0004 433/72 |
| 5,607,303 A | * | 3/1997 | Nakamura ............. | A61C 1/082 433/116 |
| 6,296,483 B1 | * | 10/2001 | Champleboux ........ | A61C 1/084 433/75 |

(Continued)

*Primary Examiner* — Nicholas Lucchesi
(74) *Attorney, Agent, or Firm* — Harness, Dickey & Pierce, P.L.C.

(57) ABSTRACT

A medical support device includes an arm having a drill attached at a tip part of the arm, a first position obtainer obtaining a representative position of the drill attached to the arm, a second position obtainer obtaining a bury start position, and a controller. The controller controls the arm and applies a burying reaction force to the drill in a burying direction, i.e., a direction from the bury start position to an inside of a implant area, when the representative position of the drill obtained by the first position obtainer is at the inside of the implant area relative to the bury start position.

18 Claims, 5 Drawing Sheets

(56) References Cited

U.S. PATENT DOCUMENTS

| | | | | |
|---|---|---|---|---|
| 6,322,567 | B1 * | 11/2001 | Mittelstadt | A61B 34/70 606/130 |
| 6,419,484 | B1 * | 7/2002 | DaSilva | A61B 5/0066 433/29 |
| 6,488,638 | B2 * | 12/2002 | Mushabac | A61C 13/0004 433/215 |
| 8,808,000 | B2 | 8/2014 | Salcedo et al. | |
| 9,283,055 | B2 * | 3/2016 | Thompson, Jr. | A61C 1/084 |
| 9,378,308 | B2 * | 6/2016 | Pieper | A61C 1/084 |
| 9,675,419 | B2 * | 6/2017 | Akeel | A61C 5/40 |
| 2002/0077542 | A1 * | 6/2002 | Vilsmeier | A61C 1/084 600/424 |
| 2002/0160337 | A1 * | 10/2002 | Klein | A61L 15/34 433/212.1 |
| 2004/0146830 | A1 * | 7/2004 | Weinstein | A61B 5/103 433/76 |
| 2004/0157188 | A1 * | 8/2004 | Luth | A61C 1/082 433/75 |
| 2005/0186533 | A1 * | 8/2005 | Cohen | A61C 1/082 433/98 |
| 2006/0127848 | A1 * | 6/2006 | Sogo | A61C 1/084 433/173 |
| 2006/0281991 | A1 * | 12/2006 | Fitzpatrick | A61B 90/16 600/426 |
| 2015/0057675 | A1 * | 2/2015 | Akeel | A61B 19/50 606/130 |
| 2016/0184068 | A1 * | 6/2016 | Chodorow | A61C 1/084 433/71 |

* cited by examiner

MEDICAL SUPPORT DEVICE

CROSS REFERENCE TO RELATED APPLICATION

The present application is based on and claims the benefit of priority of Japanese Patent Application No. 2016-002505, filed on Jan. 8, 2016, the disclosure of which is incorporated herein by reference.

TECHNICAL FIELD

The present disclosure generally relates to a medical support device that supports a medical operation by an operator.

BACKGROUND INFORMATION

As disclosed in a patent document, U.S. Pat. No. 8,808,000 B2 (patent document 1), a dental implant treatment provided as a medical operation is supported by a medical support device. The medical support device disclosed in the patent document 1 includes a multi-joint arm, a drill unit, a force sensor, and a controller.

The multi-joint arm is a device that is made up as an in-series combination of plural links connected with each other via a rotatable joint actuator. The drill unit is attached to a top end part of the multi-joint arm. The force sensor detects a force applied to the drill unit. The controller operates/controls the multi-joint arm to move the drill unit toward an operation position, according to the detected force from the force sensor.

The medical support device described above or the like has to have a safety related feature for providing an improved safety when the operator, i.e., a doctor, performs the treatment for a patient. More practically, when the conventional medical support device is used for drilling a body part of the patient, the device is expected to provide an improved safety of drilling.

SUMMARY

It is an object of the present disclosure to provide a technique of providing an improved safety for the operator in the treatment during an operation of the patient by using the medical support device.

The medical support device includes an arm, a first position obtainer, a second position obtainer, and a controller.

The arm has a drill attached at a tip of the arm. The first position obtainer obtains a representative position of the drill attached to the arm. The second position obtainer obtains a bury start position of a jawbone, and the bury start position defines an oral inside edge of a bury area that is a part of the jawbone for accepting an implant body buried in the jawbone. The bury area may also be designated as an implant area in the embodiment described below.

The controller controls the arm to apply a burying reaction force (F) to the drill, when the representative position of the drill unit obtained by the first position obtainer is at an inside of the bury area relative to the bury start position obtained by the second position obtainer. The burying reaction force is a force applied in an opposite direction relative to a burying direction of the implant body into the bury area.

According to the above, when the representative position of the drill unit obtained by the first position obtainer is an inside, or an under-surface position of the bury area relative to the bury start position is obtained by the second position obtainer, the burying reaction force is applied to the drill unit. Therefore, the drill unit drilling the jawbone has/ receives a smaller force that moves the drill unit in the burying direction of the implant body, which makes it easier to pull the drill unit out from the jawbone.

Thus, the operator operating and using the medical support device can easily pull the drill unit out from the inside of the jawbone, and the safety of the patent receiving the operation is improved.

In other words, the safety of the dental implant treatment during the implanting operation, and the safety of the medical treatment operation performed by the operator for such treatment, are improved by such medical support device.

BRIEF DESCRIPTION OF THE DRAWINGS

Objects, features, and advantages of the present disclosure will become more apparent from the following detailed description made with reference to the accompanying drawings, in which.

DETAILED DESCRIPTION

Hereafter, the embodiments of the present disclosure is described with reference to the drawings.

1. Embodiment

<1.1 Medical Support Device>

Figure 1:
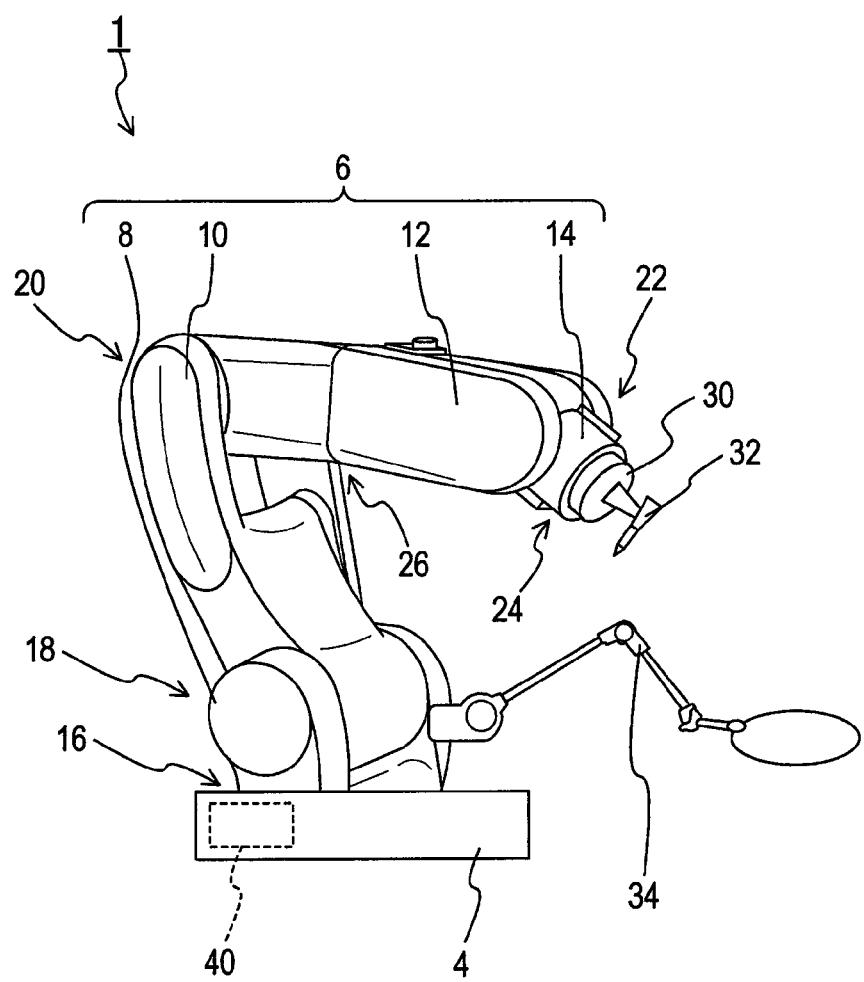
FIG. 1 is a perspective view of an appearance of a medical support device of the present disclosure.

A medical support device 1 shown in FIG. 1 is provided with a pedestal 4, an arm 6, a force detector 30, a drill unit 32, a motion sensor 34, and a robot controller 40.

The medical support device 1 is embodied substantially as a vertical articulated robot, and supports a dental implant treatment by an operator, i.e., an operation for implanting/ burying an implant body into a patient, or a jawbone. The details of a patient 60 and a jawbone 62 are described later with reference to FIG. 4 and FIG. 5.

The dental implant treatment is, more practically, a medical practice which buries an implant body in the jawbone 62 of the patient 60, and attaches a prosthetic material/tooth to the buried implant body.

In the following description, a part of the patient's 60 jawbone 62 at which the implant body is buried is designated as an implant area (i.e., a bury area in the claims). Further, an edge of the implant area facing an inside of the mouth (i.e., a "chop") is designated as a bury start position.

Note that the implant body is a fixture (i.e., an artificial root) that serves as a root of a tooth. In addition, the implant body may include not only the fixture, but an "abutment," which is a connecting member for connecting the prosthetic material (i.e., an artificial tooth).

Further, the operator is a person who performs the dental implant treatment. The operator is a medical worker, such as a dentist, a doctor, and the like for example.

The pedestal 4 is a base in which the arm 6 is installed.

The arm 6 is a vertical articulated arm provided with a base part 8, an upper arm part 10, a forearm part 12, and a hand fitting part 14.

The base part 8 is rotatably attached to the pedestal 4. The upper arm part 10 extends from the base part 8. The forearm part 12 extends from the tip of the upper arm part 10. The hand fitting part 14 is located at the tip of the forearm part 12, and holds the drill unit 32. That is, the hand fitting part 14 is equivalent to a tip part of the arm 6.

The arm 6 is provided with joint parts 16, 18, 20, 22, 24, and 26. Each of the joint parts 16, 18, 20, 22, 24, and 26 is a mechanism that connects connecting objects, i.e., two links.

The joint part 16 enables a rotation of the base part 8 about the vertical axis of the pedestal 4, i.e., about the Z-axis. The joint part 18 enables a rotation of the upper arm part 10 in a back-and-forth direction of the arm 6 relative to the base part 8.

Further, the joint part 20 enables a rotation of the forearm part 12 in an up-down direction of the arm 6 relative to the upper arm part 10. The joint part 22 enables a rotation of the hand fitting part 14 in an up-down direction of the arm 6 relative to the forearm part 12.

Furthermore, the joint part 24 enables a rotation of the hand fitting part 14 relative to the forearm part 12. The joint part 26 enables a rotation of the forearm part 12 in a twisting manner.

Figure 2:
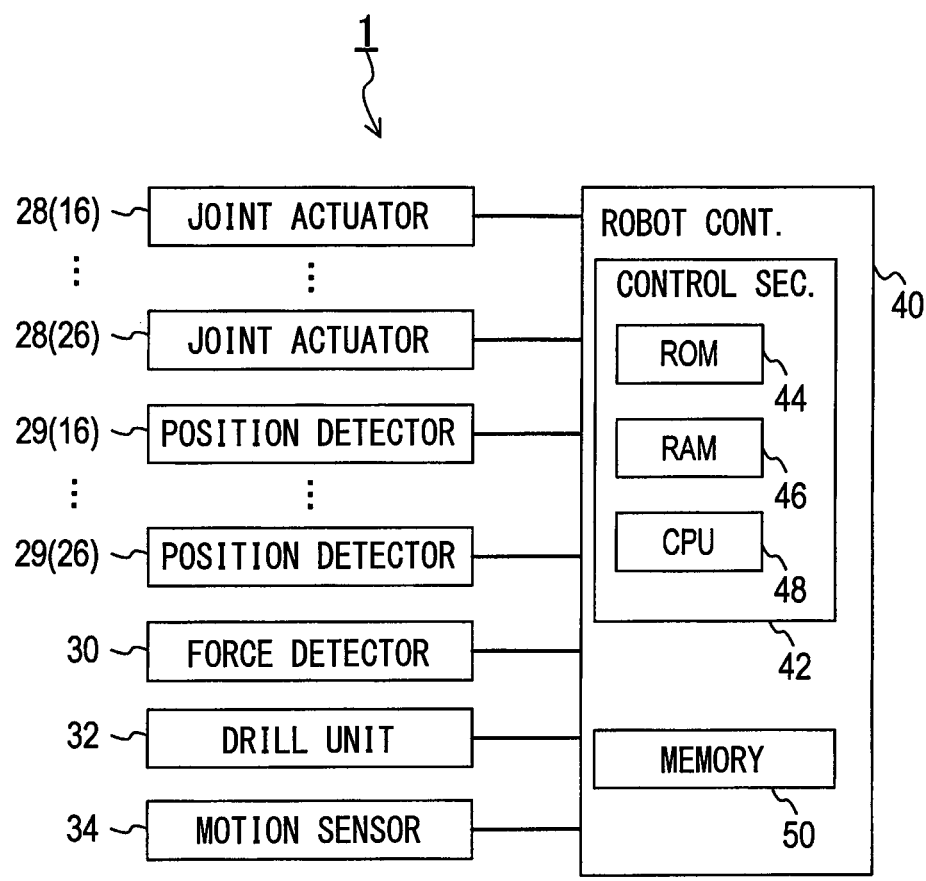
FIG. 2 is a block diagram of a control system of the medical support device.

As shown in FIG. 2, each of the joint parts 16, 18, 20, 22, 24, and 26 is provided with a joint actuator 28 and a position detector 29. The joint actuator 28 is a device that enables a rotation drive of an object. The electric motor may be considered as an example of the joint actuator 28.

The position detector 29 is a sensor that detects a degree of rotation, i.e., a shaft angle, of each joint actuator 28. The rotation encoder may be considered as an example of the position detector 29.

The shaft angle, may be an angle by which the shaft of the joint actuator 28 is rotated, and the shaft angle may be a relative angle with reference to a certain reference angle that is set as a standard in advance, or may be an absolute angle.

That is, the arm 6 is a mechanism that enables a movement of the drill unit 32, and is the vertical articulated arm that is made up as a combination of the multiple links connected via the rotatable joint parts.

Note that the link described above is a member of the arm 6, and is considered as a rigid body. The links in the present embodiment are the base part 8, the upper arm part 10, the forearm part 12, and the hand fitting part 14.

The force detector 30 is a sensor installed in a tip part, i.e., in the hand fitting part 14, of the arm 6. The force detector 30 detects a magnitude and a direction of the force which are applied to the tip part of the arm 6. As the force detector 30, an electric capacity-type force sensor may be used, or a strain gauge-type force sensor may be used, for example. Further, the force described above includes a force that is caused by the movement of the drill unit 32, which is an operation of the drill unit 32 by the operator.

The drill unit 32 is a tool for performing the dental implant treatment. The drill unit 32 includes various kinds of drill bit used for dental treatment, and a drill drive mechanism for driving the drill bit. The drill unit 32 includes a so-called dental handpiece. The dental handpiece in such case includes a straight-geared angle handpiece and a contra hand piece.

The drill unit 32 is attached to the hand fitting part 14 via the force detector 30. That is, the drill unit 32 is attached to a tip part of the arm 6.

The motion sensor 34 is a device that specifies a relative position relationship between (i) a reference point predefined as a point of the medical support device 1 and (ii) an affected part of the patient 60. The position of the affected part of the patient 60 identified by the motion sensor 34 is matched with the bury start position. Then, while the operator performs the dental implant treatment, the motion sensor 34 tracks the bury start position.

The robot controller 40 is provided with a control section (i.e., a controller) 42 and a memory 50, and drives the joint actuators 28 of the arm 6.

The control section 42 is a control device having a microcomputer together at least with a Read-only Memory (ROM) 44, a Random Access Memory (RAM) 46, and a Central Processing Unit (CPU) 48. The memory 50 is a device that memorizes information and data.

The control section 42 identifies a representative position of the tip part of the arm 6, i.e., the drill unit 32, according to the detection result of each of the position detectors 29. The representative position described above means a "typical" position, or a position representing the drill unit 32 as a whole, for example.

An example of the representative position may be a position of the tip part of the unit 32, a position of the center of gravity of the unit 32, a position of a predetermined specific part, or the like.

In the present embodiment, a representative position of the drill unit 32 is assumed to be a tip part of the drill bit of the drill unit 32.

The memory 50 memorizes a processing program for the robot controller 40 to perform a medical support process. The medical support process is a process that supports an act or acts of the operator by driving the arm 6, which includes a gripping act for gripping the drill unit 32 and a drilling act for drilling the jawbone 62 of the patient 60. Note that the drilling described above means boring a hole in the jawbone 62 by using the drill unit 32, for implanting/burying the implant body.

<1.2 Medical Support Process>

Next, the medical support process which is performed by the robot controller 40 is described.

The medical support process concerned starts upon receiving an input of a start instruction for starting the medical support process.

Figure 3:
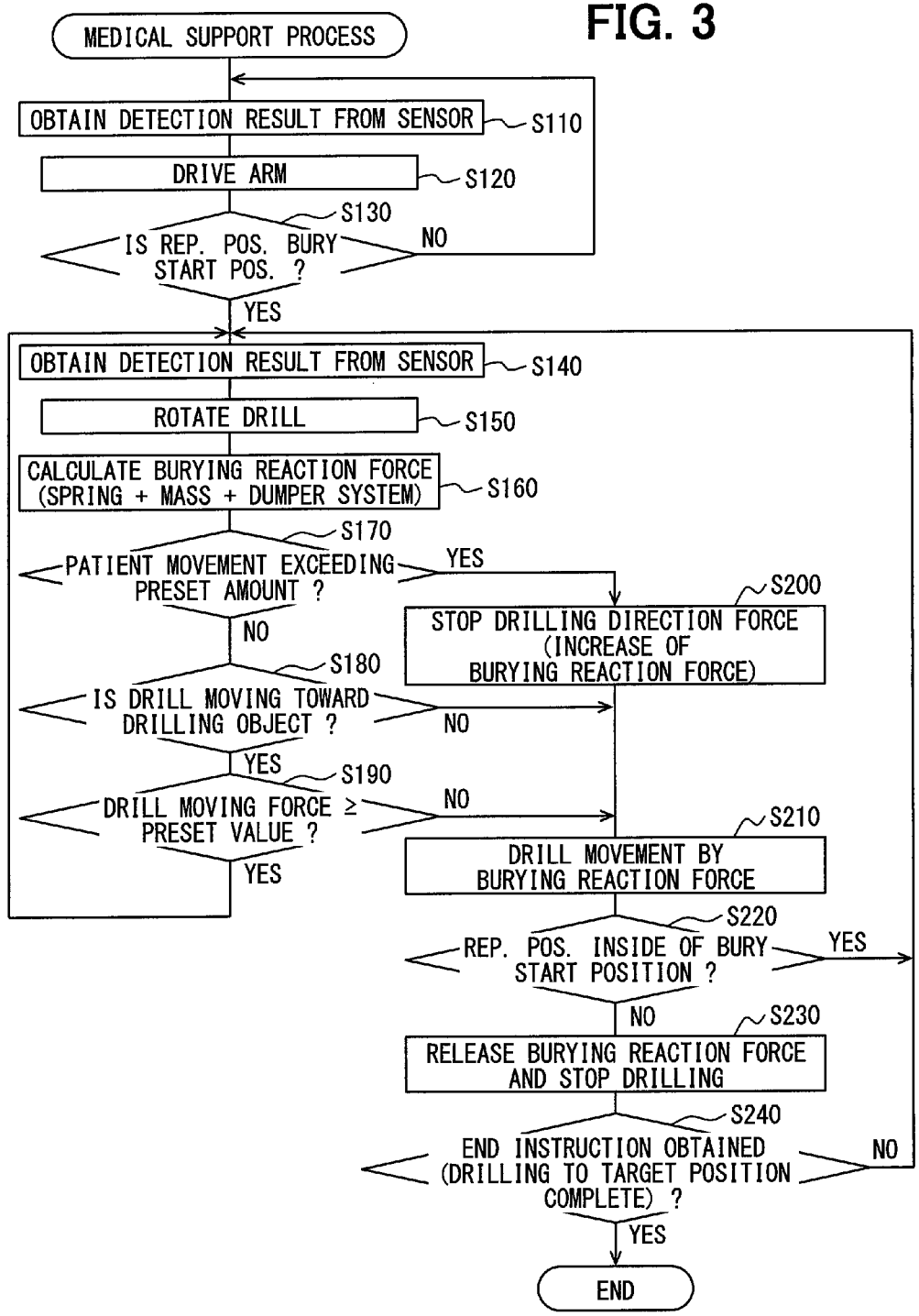
FIG. 3 is a flowchart of a procedure of a medical support process.

Then, at a time of starting of the medical support process, as shown in FIG. 3, the robot controller 40 obtains a detection result from each of the force detector 30, the position detector 29, and of the motion sensor 34 (S110).

That is, in S110, the robot controller 40 obtains detection results, i.e., (i) the direction of movement and the magnitude of the force applied to the drill unit 32 detected by the force detector 30, and (ii) the bury start position detected by the motion sensor 34, and (iii) a detection result of the position detector 29.

Then, the control section 42 of the robot controller 40 identifies the representative position of the drill unit 32 according to the detection result of each of the position detectors 29. The identification method of the representative position may be, for example, performed by adding a length of the drill unit 32 from the reference position to the representative position to the position of the tip part of the arm 6 identified by a method.

The medical support process, i.e., the robot controller 40, drives the arm 6 according to the magnitude and the direction of the force for the movement of the drill unit 32 obtained in S110 (S120).

Then, the robot controller 40 determines whether the representative position of the drill unit 32 identified in S110 matches, i.e., is identical to, the bury start position, which obtained in S110 (S130).

The "matching" of the two positions means not only a complete matching in which no difference (i.e., zero difference) is observed between the representative position of the drill unit 32 and the bury start position, but also a substantial matching in which a difference therebetween is nominal, i.e., is recognizable as substantially equal to zero.

When the representative position of the drill unit 32 is not in agreement, i.e., not matching, with the bury start position as a result of the determination in S130 (S130: NO), the robot controller 40 returns the medical support process to S110, and drives the arm 6 until the representative position of the drill unit 32 matches with the bury start position.

On the other hand, when the representative position of the drill unit 32 is matching with the bury start position as a result of the determination in S130 (S130: YES), the robot controller 40 again obtains the detection result of each of the force detector 30, the position detector 29, and the motion sensor 34 (S140).

That is, in S140, the robot controller 40 obtains the magnitude of the force and the direction of movement of the drill unit 32 that is being moved by the operator detected at such moment by the force detector 30, the bury start position detected by the motion sensor 34, and the representative position of the drill unit 32.

Then, the medical support process, i.e., the robot controller 40, rotates the drill bit of the drill unit 32 (S150).

Then, the robot controller 40 calculates, or identifies, a burying reaction force F, and adds, i.e., applies, the force to the arm 6 (S160). In S160, the robot controller 40 may calculate the burying reaction force F based on the vibration model of mass, spring, and damper system shown in a following equation (1).

$$F = kx + c\dot{x} + m\ddot{x} \quad \text{[Equation 1]}$$

In the equation (1), the term x represents an amount of displacement of the representative position of the drill unit 32 from the bury start position to the inside of the implant area. The term $\dot{x}$ represents a time differential of the amount of displacement of the representative position of the drill unit 32 from the bury start position to the inside of the implant area. The term $\ddot{x}$ represents the second degree differential of the amount of displacement of the representative position of the drill unit 32 from the bury start position to the inside of the implant area from time. Further, the constant k represents a spring modulus defined in advance, the constant c represents a damping coefficient defined in advance, and the constant m represents a mass of the drill unit 32.

Thereby, in S160, the robot controller 40 adds a greater burying reaction force F to the arm 6, as the amount of displacement from the bury start position to the inside of the implant area increases.

Then, the medical support process, i.e., the robot controller 40, determines whether the displacement of the bury start position, i.e., a movement of the patient 60, is equal to or greater than a preset amount set in advance (S170).

When the movement of the patient 60 is equal to or greater than the preset amount as a result of the determination (S170: YES), the robot controller 40 shifts the medical support process to S200 that is mentioned later in detail.

On the other hand, when the movement of the patient 60 or less than the preset amount as a result of the determination in S170 (S170: NO), the robot controller 40 shifts the medical support process to S180.

In the S180, the robot controller 40 determines whether the movement direction of the drill unit 32 by the operator is a drilling direction of the drilling object (S180). The drilling direction for drilling the drilling object described above is a direction of movement for moving the drill unit 32 from the bury start position to the inside of the implant area.

When the movement direction of the drill unit 32 is not the drilling direction as a result of determination in S180 (S180: NO), the robot controller 40 shifts the medical support process to S210 mentioned later in detail.

On the other hand, when the movement direction of the drill unit 32 is the drilling direction as a result of determination in S180 (S180: YES), the robot controller 40 shifts the medical support process to S190.

In S190, the robot controller 40 determines whether a force with which the drill unit 32 is moved by the operator is equal to or greater than a preset value defined in advance.

When the force of S190 with which the drill unit 32 is moved is equal to or greater than preset value as a result of the determination in S190 (S190: YES), the robot controller 40 returns the medical support process to S140.

On the other hand, when the force of S190 with which the drill unit 32 is moved is less than the preset value as a result of the determination in S190 (S190: NO), the robot controller 40 shifts the medical support process to S210.

Note that, in S200, which is subsequent to a YES determination in S170, i.e., when the movement of the patient 60 is equal to or greater than the preset amount, the robot controller 40 performs a safety control. The safety control described above is a control that improves the safety of the dental implant treatment.

More concretely, in S200, the robot controller 40 stops, as a safety control, the drive of the arm 6 in the drilling direction from the bury start position to the inside of the implant area. Further, in S200, the robot controller 40 provides, as the safety control, a greater burying reaction force F added to the arm 6. That is, in S200, the force for moving the arm 6 in the drilling direction is stopped, and the burying reaction force F added to the arm 6 is increased.

Then, in S210, the robot controller 40 moves the arm 6 in an opposite direction that is opposite to the drilling direction from the bury start position to the inside of the implant area, according to the burying reaction force F. The opposite direction described above means a direction along an axis of the implant body that is buried at the bury start position into the jawbone 62 of the patient 60, from the implant body into a hollow space in the mouth of the patient 60.

Further, the medical support process, i.e., the robot controller 40, determines whether the representative position of the drill unit 32 is inside of the implant area relative to the bury start position (S220).

When the representative position of the drill unit 32 is inside of the implant area relative to the bury start position as a result of the determination in S220 (S220: YES), the robot controller 40 returns the medical support process to S140.

On the other hand, when the representative position of the drill unit 32 is outside of the bury start position, i.e., on a safe side of the dental implant treatment, as a result of determination in S220 (S220: NO), the robot controller 40 shifts the medical support process to S230.

In S230, the robot controller 40 releases addition, i.e., application, of the burying reaction force F to the arm 6. Further, in S230, the robot controller 40 stops the rotation of the drill bit of the drill unit 32.

The robot controller 40 then determines whether the drilling has reached to a planned burying depth, i.e., to a target position (S240). In S240, the robot controller 40 may determine that the drilling has reached to the planned burying depth when receiving a drilling end instruction. The drilling end instruction may be received by an operation of a switch or the like. The switch for receiving the drilling end instruction may be a dedicated switch for receiving such an instruction, or a switch that may be shared with other operations. The switch for receiving the drilling end instruction may be, for example, a drill bit drive switch for driving the drill bit of the drill unit 32, which is used as a dental treatment/operation.

When drilling has not reached to the planned burying depth as a result of determination in S240 (S240: NO), the robot controller 40 returns the medical support process to S230.

On the other hand, when the drilling has reached to the planned burying depth as a result of determination in S240 (S240: YES), the robot controller 40 ends the medical support process.

When ending the medical support process, the robot controller 40 may control the drill unit 32 so that the tip part of the drill unit 32 moves out of the mouth of the patient 60 along a preset instrument movement path.

Figure 4:
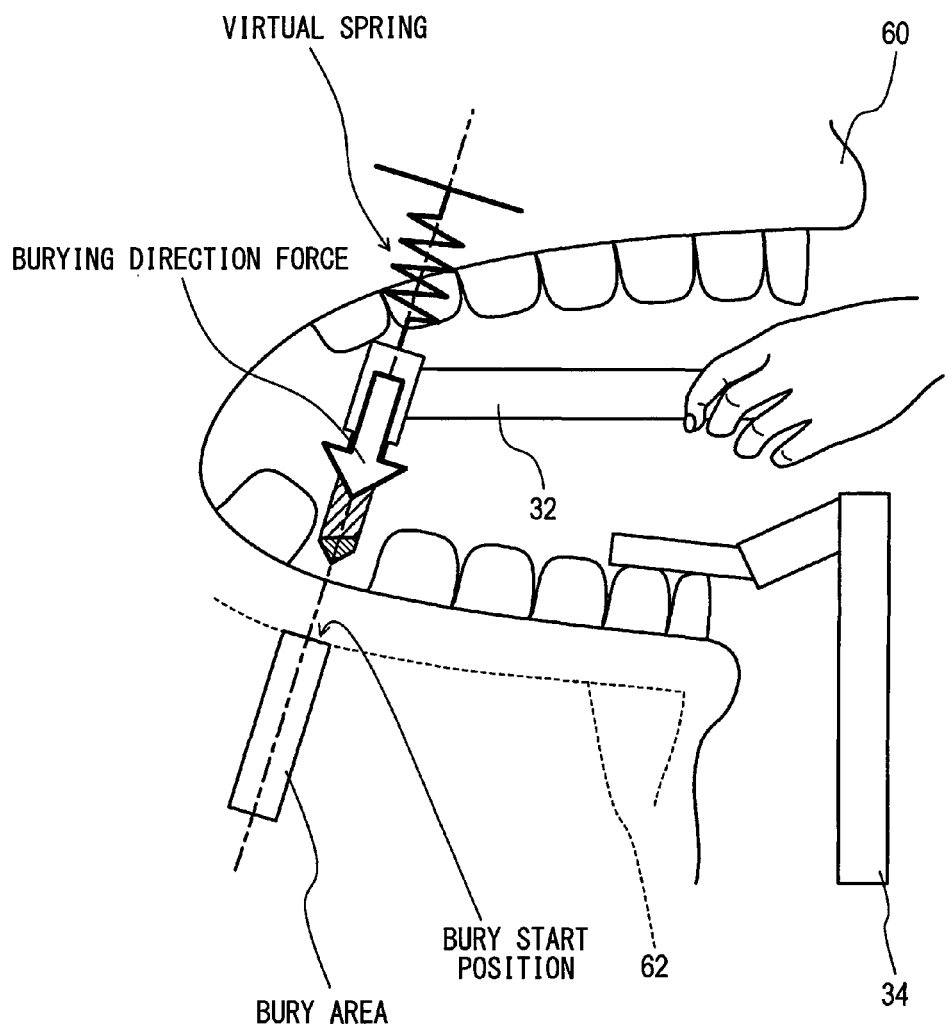
FIG. 4 is an illustration of contents of the medical support process.

That is, more practically, when the operator moves the drill unit 32 from the bury start position toward an inside of the implant area, the medical support process supports, as shown in FIG. 4, the dental implant treatment by the operator who is holding/gripping the drill unit 32 by driving the arm 6.

Figure 5:
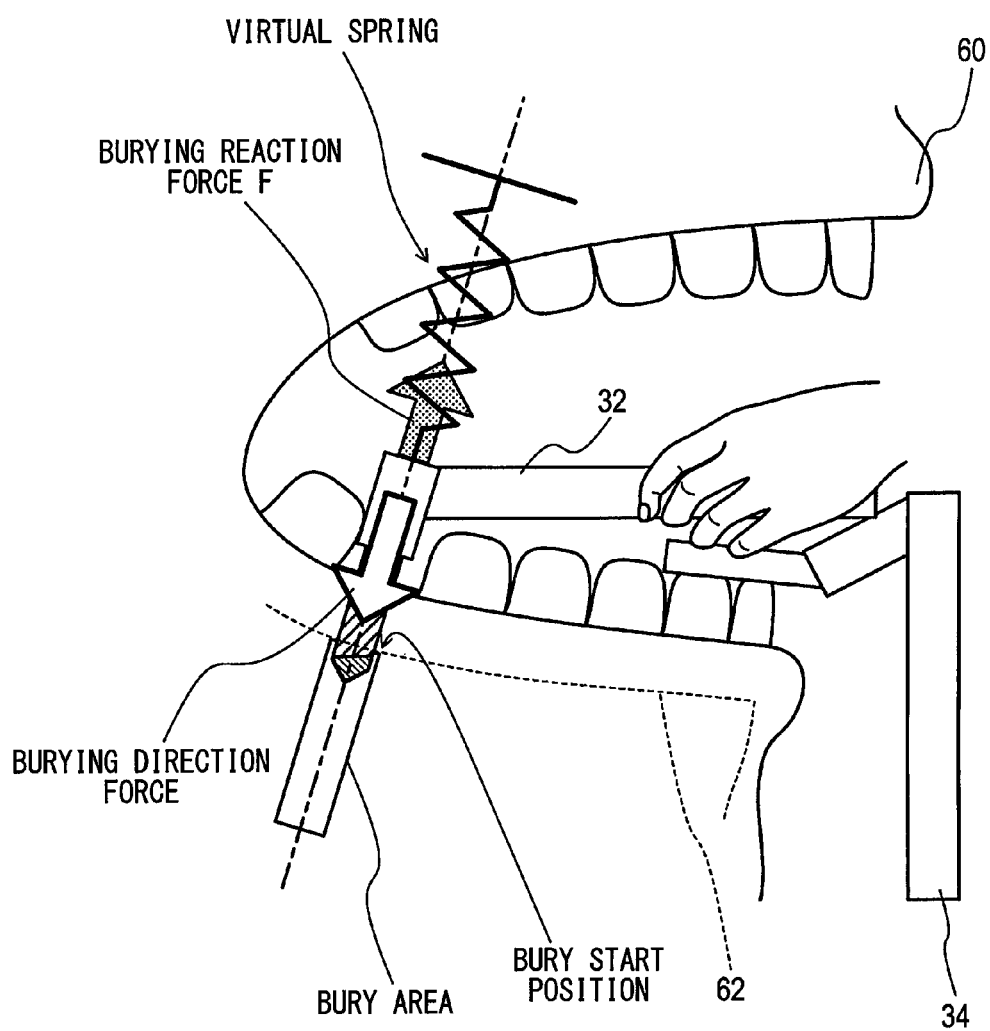
FIG. 5 is an illustration of an operation of a burying reaction force.

As shown in FIG. 5, when the drill bit of the drill unit 32 is rotated and the drilling of the jawbone 62 in the implant area is performed, the support described above is provided by applying the burying reaction force F to the arm 6.

The application direction of the burying reaction force F is an opposite direction that is opposite to a direction from the bury start position into (i.e., to/toward the inside of) the implant area.

Therefore, when the force with which the operator moves the drill unit 32 for drilling the jawbone 62 becomes smaller than the burying reaction force F, the drill unit 32 is easily pulled out from the jawbone thanks to, with the help of, the burying reaction force F.

2. Effects of the Present Embodiment (2.1) As described above, the operator using the medical support device 1 can pull the drill unit 32 easily out from the jawbone 62, enabling an easy implementation of a safety for the patient 60.

That is, according to the medical support device 1 described above, the safety of the dental implant treatment for the patient 60, and the safety of the operation/treatment performed by the operator are improved.

(2.2) In the medical support process, an application period for applying the burying reaction force F to the drill unit 32 is set as a period during which the drill unit 32 is moved to the inside of the implant area from, i.e., relative to, the bury start position.

That is, according to the medical support device 1, when the operator performs the drilling in the dental implant treatment, the burying reaction force is applied to the drill unit 32 all the time, and the safety of the dental implant treatment to the patient 60 is thus further improved.

(2.3) Furthermore, in the medical support process, when the patient 60 moves during operation of the dental implant treatment by the operator, the safety control is performed. One of such a safety control performed by the medical support process is the stop of the drive of the arm 6 in the drilling direction, which is a direction of drilling into the implant area of the jawbone 62 from the bury start position.

Thereby, according to the medical support device 1, the drill unit 32 is easily pulled out, i.e., comes out, from the jawbone 62.

(2.4) Further, in the above-mentioned medical support process, as another safety control, the burying reaction force F is increased.

Thereby, according to the medical support device 1, it is easier for the drill unit 32 to be pulled out from the jawbone 62 at an early timing of such operation.

As the results of the above-described effects, the medical support device 1 is enabled to provide an improved safety of the dental implant treatment for the patient 60.

(2.5) Furthermore, in the medical support process, the magnitude of the burying reaction force F is calculated as a greater value for an application to the arm 6, as the burying depth of the drill unit 32 into the bury area increases, i.e., as the displacement of the drill unit 32 in the bury area increases.

Thereby, according to the medical support device 1, the burying reaction force F of a suitable magnitude according to the burying depth of the drill unit 32 into the jawbone 62 is applicable to the arm 6.

(2.6) Furthermore, the burying reaction force F in the medical support process is calculated based on the vibration model of mass, spring, and damper system.

Specifically, due to a built-in damper model included in the equation of the burying reaction force F, the medical support device 1 is enabled to quickly prevent/control the vibration of the drill unit 32 at an early timing, when the drill unit 32 is pulled out from the jawbone 62.

3. Other Embodiments

Although the present disclosure has been described in connection with preferred embodiment thereof with reference to the accompanying drawings, it is to be noted that various changes and modifications will become apparent to those skilled in the art.

(3.1) For example, the implant area may also be located in the upper jawbone, although the implant area described in FIG. 4 and FIG. 5 is located in the lower jawbone in the above-mentioned embodiment of the present disclosure.

(3.2) In S160 of the above-mentioned embodiment, although the burying reaction force F is calculated based on the vibration model of mass, spring, and damper system, the calculation method of the burying reaction force F is not limited thereto.

For example, the burying reaction force F may be calculated based on the model of spring and damper system, and the burying reaction force F may also be calculated based on the spring system model. The burying reaction force F may also be calculable by the other methods.

(3.3) In the above-mentioned embodiment, although the medical support device 1 is provided with the vertical articulated arm as the arm 6, the arm 6 of the medical support device 1 needs not be limited to such type.

For example, the medical support device 1 may be provided with a horizontal articulated arm as the arm 6, or may be provided with the other types of arms as the arm 6.

(3.4) Some or all of the functions that are performed by the robot controller 40 in the above-mentioned embodiment may be provided by hardware of one or more ICS (i.e., Integrated Circuits) or the like.

(3.5) In the above-mentioned embodiment, although the program is stored in the memory 50, the storage media for storing the program is not restricted to such device, and the program may be stored in a non-transitive tangible storage devices, e.g., in a semiconductor memory or the like.

(3.6) The control section 42 may execute the program stored in the non-transitive tangible storage medium. The method corresponding to such program is realized by the execution of such program.

(3.7) The embodiment of the present disclosure may be provided by omitting a part of the above-described embodiment. The embodiment of the present disclosure may be provided as a combination of the above-mentioned embodiment and a modification thereof.

Such changes, modifications, and summarized schemes are to be understood as being within the scope of the present disclosure as defined by appended claims.

(3.8) In addition, the numerals in the parenthesis written in the claims and the summary are not limiting the scope of the claimed contents, i.e., are provided as an example relationship between the claims and the embodiments.

(3.9) The present disclosure is realizable in the various forms, e.g., as a program that is executed by a computer for supporting the dental implant treatment, as a control method of the arm, or the like.

4. Exemplary Relationship

The function obtained by performing S110, S140 of the medical support process is equivalent to the first position obtainer and the second position obtainer in the claims.

The function obtained by performing S130, S160, S180, S190, and S220 is equivalent to the controller in the claims.

The function obtained by performing S170 and S200 is equivalent to the safety controller in the claims.

What is claimed is:

1. A medical support device comprising:
an arm having a drill that is attached at a tip part of the arm;
a first position obtainer configured to obtain a representative position of the drill attached to the arm;
a second position obtainer configured to obtain a bury start position of a jawbone, the bury start position defining an oral inside edge of an implant area that is a part of the jawbone for accepting an implant body buried in the jawbone; and
a controller configured to control the arm to apply a burying reaction force to the drill, the burying reaction force applied in an opposite direction relative to a burying direction of the implant body into the implant area of the jawbone, when the representative position of the drill obtained by the first position obtainer is at an inside of the implant area relative to the bury start position obtained by the second position obtainer, wherein
the controller calculates a magnitude of the burying reaction force by multiplying a displacement amount of the representative position of the drill from the bury start position to the inside of the implant area by a predetermined spring modulus.

2. The medical support device of claim 1 further comprising:
a force detector disposed at the tip part of the arm and configured to detect a force applied to the drill, wherein
the controller controls the arm to apply the burying reaction force to the drill, when the force detector detects a force in a direction from the bury start position to the inside of the implant area.

3. The medical support device of claim 2, wherein
the controller applies a greater burying reaction force to the drill, as the force detected by the force detector that forces an object from the bury start position to the inside of the implant area increases.

4. The medical support device of claim 1, wherein
the second position obtainer repeatedly obtains the bury start position, and
the controller has a safety controller configured to perform a safety control to improve safety of a dental implant treatment, when an amount of change of the bury start position after repeatedly obtaining the bury start position is greater than a preset standard amount.

5. The medical support device of claim 4, wherein
the safety controller stops, as the safety control, a drive of the arm in a direction from the bury start position to the inside of the implant area.

6. The medical support device of claim 4, wherein
the safety controller increases, as the safety control, the burying reaction force.

7. A medical support device comprising:
an arm having a drill that is attached at a tip part of the arm;
a first position obtainer configured to obtain a representative position of the drill attached to the arm;
a second position obtainer configured to obtain a bury start position of a jawbone, the bury start position defining an oral inside edge of an implant area that is a part of the jawbone for accepting an implant body buried in the jawbone; and
a controller configured to control the arm to apply a burying reaction force to the drill, the burying reaction force applied in an opposite direction relative to a burying direction of the implant body into the implant area of the jawbone, when the representative position of the drill obtained by the first position obtainer is at an inside of the implant area relative to the bury start position obtained by the second position obtainer, wherein
the controller calculates a magnitude of the burying reaction force as a sum of a first multiplication result and a second multiplication result, wherein
the first multiplication result is a product of a displacement amount of the representative position of the drill from the bury start position to the inside of the implant area and a predetermined spring coefficient, and wherein
the second multiplication result is a product of a derivative of the displacement amount with respect to time and a predetermined damping coefficient.

8. The medical support device of claim 7 further comprising:
a force detector disposed at the tip part of the arm and configured to detect a force applied to the drill, wherein
the controller controls the arm to apply the burying reaction force to the drill, when the force detector detects a force in a direction from the bury start position to the inside of the implant area.

9. The medical support device of claim 8, wherein the controller applies a greater burying reaction force to the drill, as the force detected by the force detector that forces an object from the bury start position to the inside of the implant area increases.

10. The medical support device of claim 7, wherein the second position obtainer repeatedly obtains the bury start position, and the controller has a safety controller configured to perform a safety control to improve safety of a dental implant treatment, when an amount of change of the bury start position after repeatedly obtaining the bury start position is greater than a preset standard amount.

11. The medical support device of claim 10, wherein the safety controller stops, as the safety control, a drive of the arm in a direction from the bury start position to the inside of the implant area.

12. The medical support device of claim 10, wherein the safety controller increases, as the safety control, the burying reaction force.

13. A medical support device comprising:

an arm having a drill that is attached at a tip part of the arm;

a first position obtainer configured to obtain a representative position of the drill attached to the arm;

a second position obtainer configured to obtain a bury start position of a jawbone, the bury start position defining an oral inside edge of an implant area that is a part of the jawbone for accepting an implant body buried in the jawbone; and a controller configured to control the arm to apply a burying reaction force to the drill, the burying reaction force applied in an opposite direction relative to a burying direction of the implant body into the implant area of the jawbone, when the representative position of the drill obtained by the first position obtainer is at an inside of the implant area relative to the bury start position obtained by the second position obtainer, wherein the controller calculates a magnitude of the burying reaction force as a sum of a first multiplication result, a second multiplication result, and a third multiplication result, wherein the first multiplication result is a product of a displacement amount of the representative position of the drill from the bury start position to the inside of the implant area and a predetermined spring coefficient, and wherein the second multiplication result is a product of a first derivative of the displacement amount with respect to time and a predetermined damping coefficient, and wherein the third multiplication result is a product of a second derivative of the displacement amount with respect to time and a mass of the drill.

14. The medical support device of claim 13 further comprising:

a force detector disposed at the tip part of the arm and configured to detect a force applied to the drill, wherein the controller controls the arm to apply the burying reaction force to the drill, when the force detector detects a force in a direction from the bury start position to the inside of the implant area.

15. The medical support device of claim 14, wherein the controller applies a greater burying reaction force to the drill, as the force detected by the force detector that forces an object from the bury start position to the inside of the implant area increases.

16. The medical support device of claim 13, wherein the second position obtainer repeatedly obtains the bury start position, and the controller has a safety controller configured to perform a safety control to improve safety of a dental implant treatment, when an amount of change of the bury start position after repeatedly obtaining the bury start position is greater than a preset standard amount.

17. The medical support device of claim 16, wherein the safety controller stops, as the safety control, a drive of the arm in a direction from the bury start position to the inside of the implant area.

18. The medical support device of claim 16, wherein the safety controller increases, as the safety control, the burying reaction force.

\* \* \* \* \*